(12) United States Patent
Lorimer et al.

(10) Patent No.: US 7,652,139 B2
(45) Date of Patent: Jan. 26, 2010

(54) CLOPIDOGREL SALT AND POLYMORPHIC FORMS THEREOF

(75) Inventors: Keith Richard Lorimer, West Lafayette, IN (US); Alicia Tee Fuay Ng, West Lafayette, IN (US)

(73) Assignee: sanofi-aventis, Paris (FR)

( * ) Notice: Subject to any disclaimer, the term of this patent is extended or adjusted under 35 U.S.C. 154(b) by 0 days.

(21) Appl. No.: 11/550,865

(22) Filed: Oct. 19, 2006

(65) Prior Publication Data

US 2007/0088048 A1 Apr. 19, 2007

Related U.S. Application Data

(63) Continuation of application No. PCT/US2005/013279, filed on Apr. 18, 2005.

(60) Provisional application No. 60/563,795, filed on Apr. 20, 2004.

(51) Int. Cl.
C07D 495/04 (2006.01)
A61K 31/4365 (2006.01)

(52) U.S. Cl. ................ 546/114; 514/301

(58) Field of Classification Search ............ 546/15, 546/114
See application file for complete search history.

(56) References Cited

U.S. PATENT DOCUMENTS

| 4,847,265 A | 7/1989 | Badorc |
| 6,429,210 B1 | 8/2002 | Bosquet et al. |
| 2003/0225129 A1 | 12/2003 | Lifshitz-Liron et al. |
| 2005/0113406 A1 | 5/2005 | Nagy et al. |
| 2005/0256152 A1 | 11/2005 | Doser et al. |
| 2006/0264636 A1 | 11/2006 | Lohray et al. |

FOREIGN PATENT DOCUMENTS

| WO | WO 2005/026174 | 3/2005 |
| WO | WO 2005/048992 | 6/2005 |
| WO | WO 2005/068471 | 7/2005 |
| WO | WO 2005/080890 | 9/2005 |

OTHER PUBLICATIONS

Britian, et al., Polymorphism in Pharmaceutical Solids Passage, Polymorphism in Pharmaceutical Solids; 1999; pp. 235-238.
Caira M R, Crystalline Polymorphism of Organic Compounds, Topics in Current Chemistry, Springer, Berlin, Germany; vol. 198, 1998, pp. 163-208.

*Primary Examiner*—Ardin Marschel
*Assistant Examiner*—Meghan Finn
(74) *Attorney, Agent, or Firm*—Brian R. Morrill

(57) ABSTRACT

The invention relates to methyl(+)-(S)-α-(2-chlorophenyl)-6,7-dihydrothieno[3,2-C]pyridine-5(4H) acetate naphthalene-1,5-disulfonate or a polymorphic form and/or a hydrate and/or a solvate thereof, to pharmaceutical compositions containing the same, and to the method of use thereof for inhibiting platelet aggregation.

1 Claim, 12 Drawing Sheets

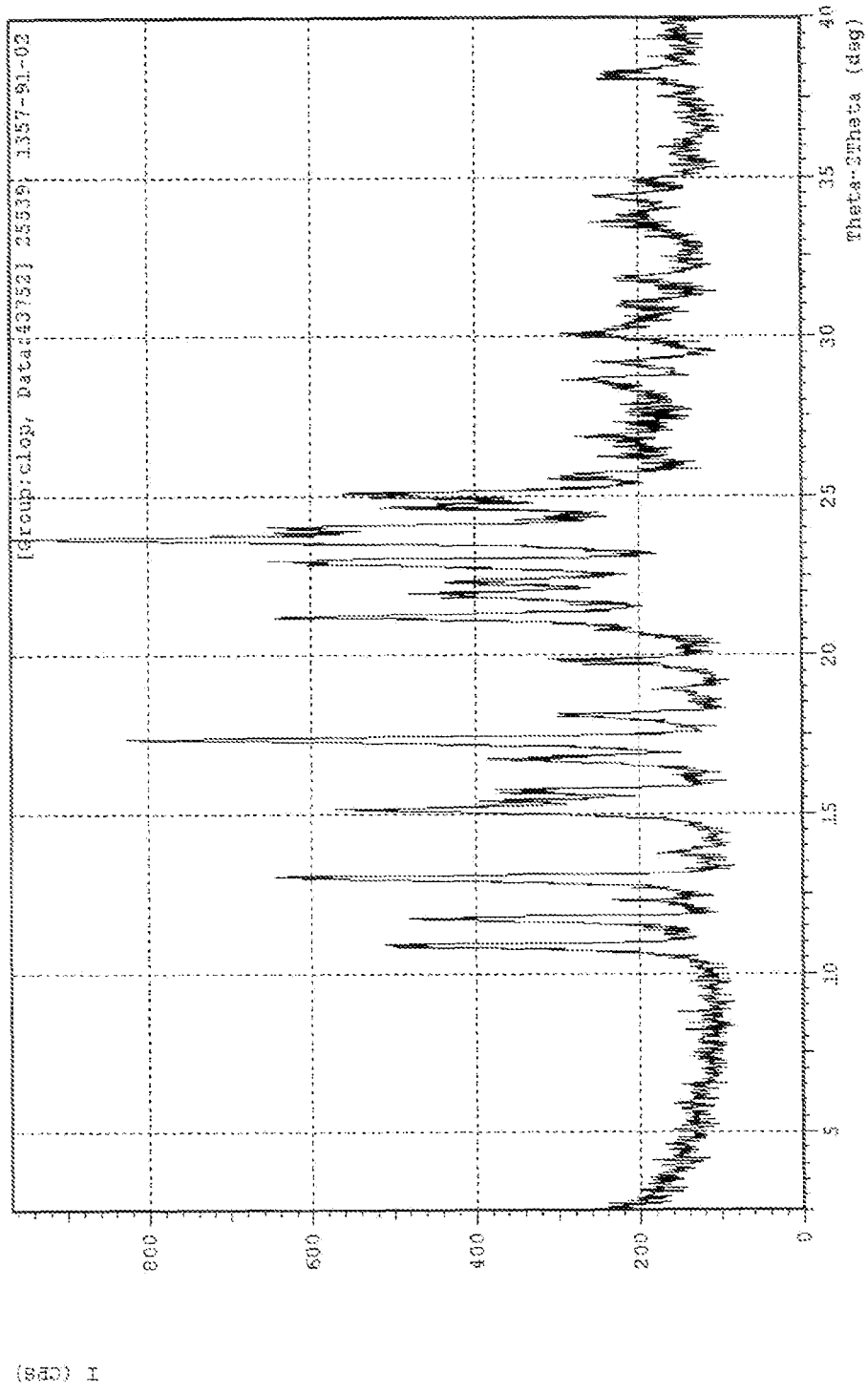
Figure 1A. XRPD pattern of Form A of methyl(+)-(S)-α-(2-chlorophenyl)-6,7-dihydrothieno[3,2-C]pyridine-5(4H) acetate naphthalene-1,5-disulfonate

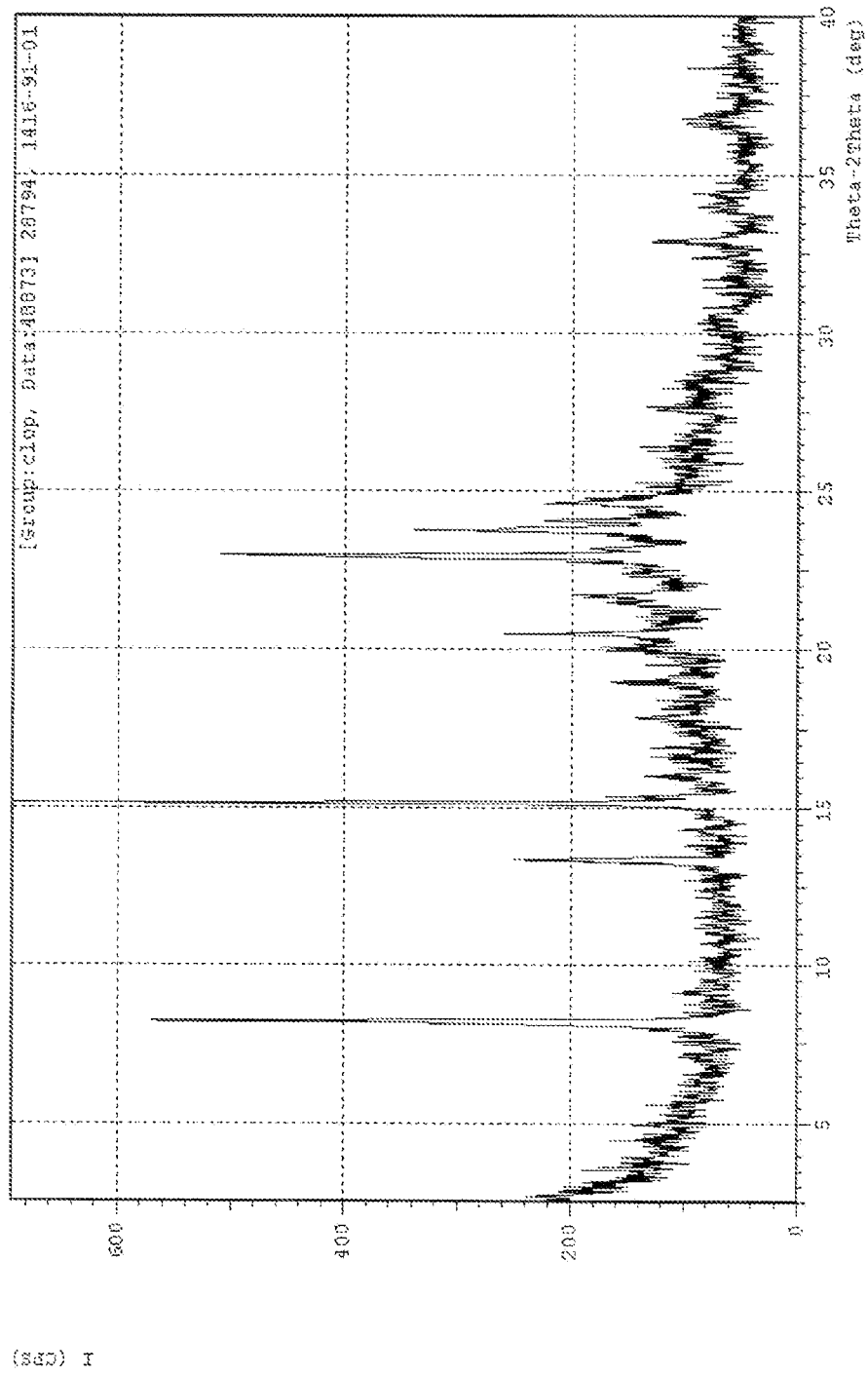
Figure 1B. XRPD pattern of Form B of methyl(+)-(S)-α-(2-chlorophenyl)-6,7-dihydrothieno[3,2-C]pyridine-5(4H) acetate naphthalene-1,5-disulfonate

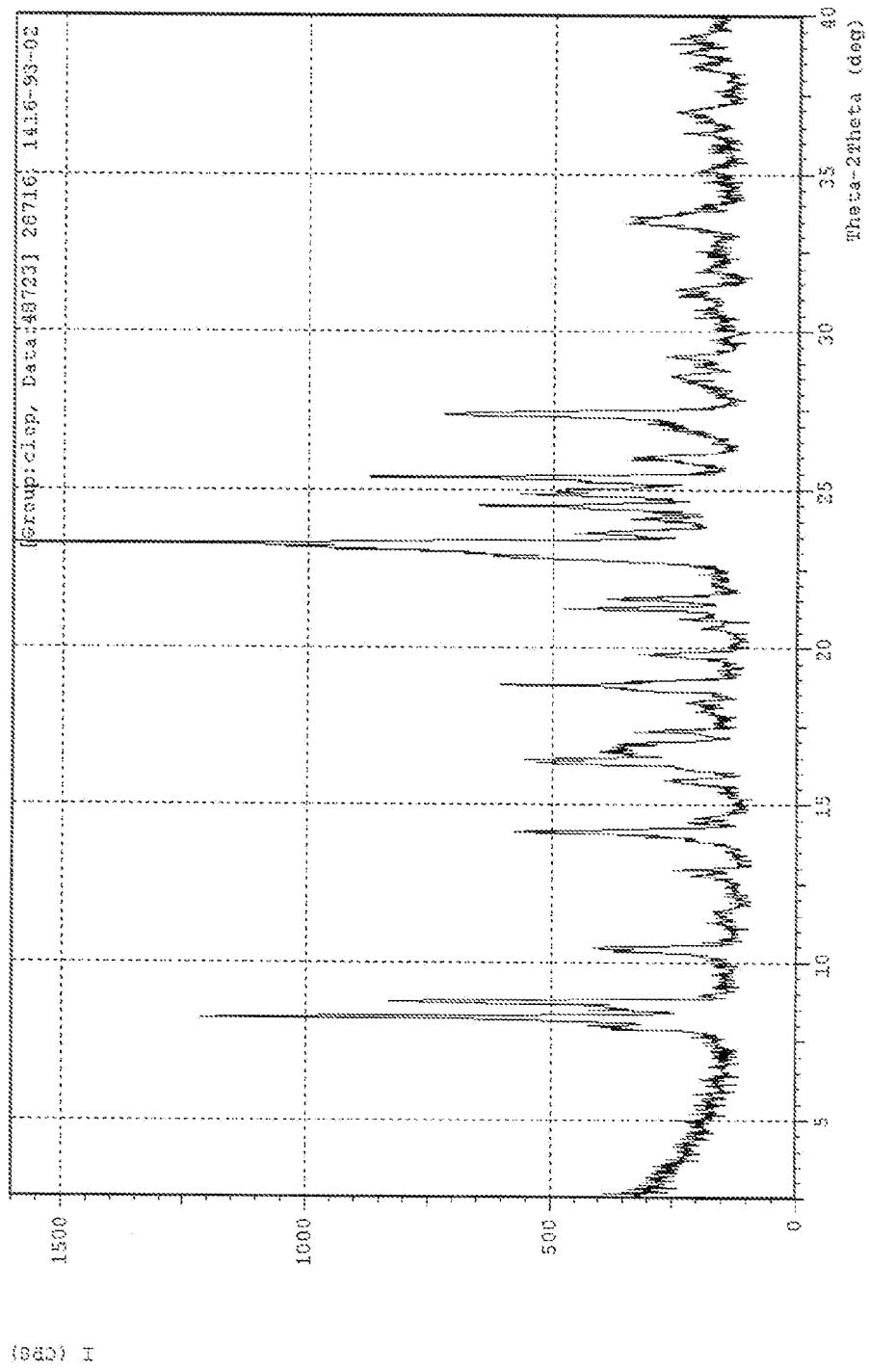
Figure 1C. XRPD pattern of Form C of methyl(+)-(S)-α-(2-chlorophenyl)-6,7-dihydrothieno[3,2-C]pyridine-5(4H) acetate naphthalene-1,5-disulfonate

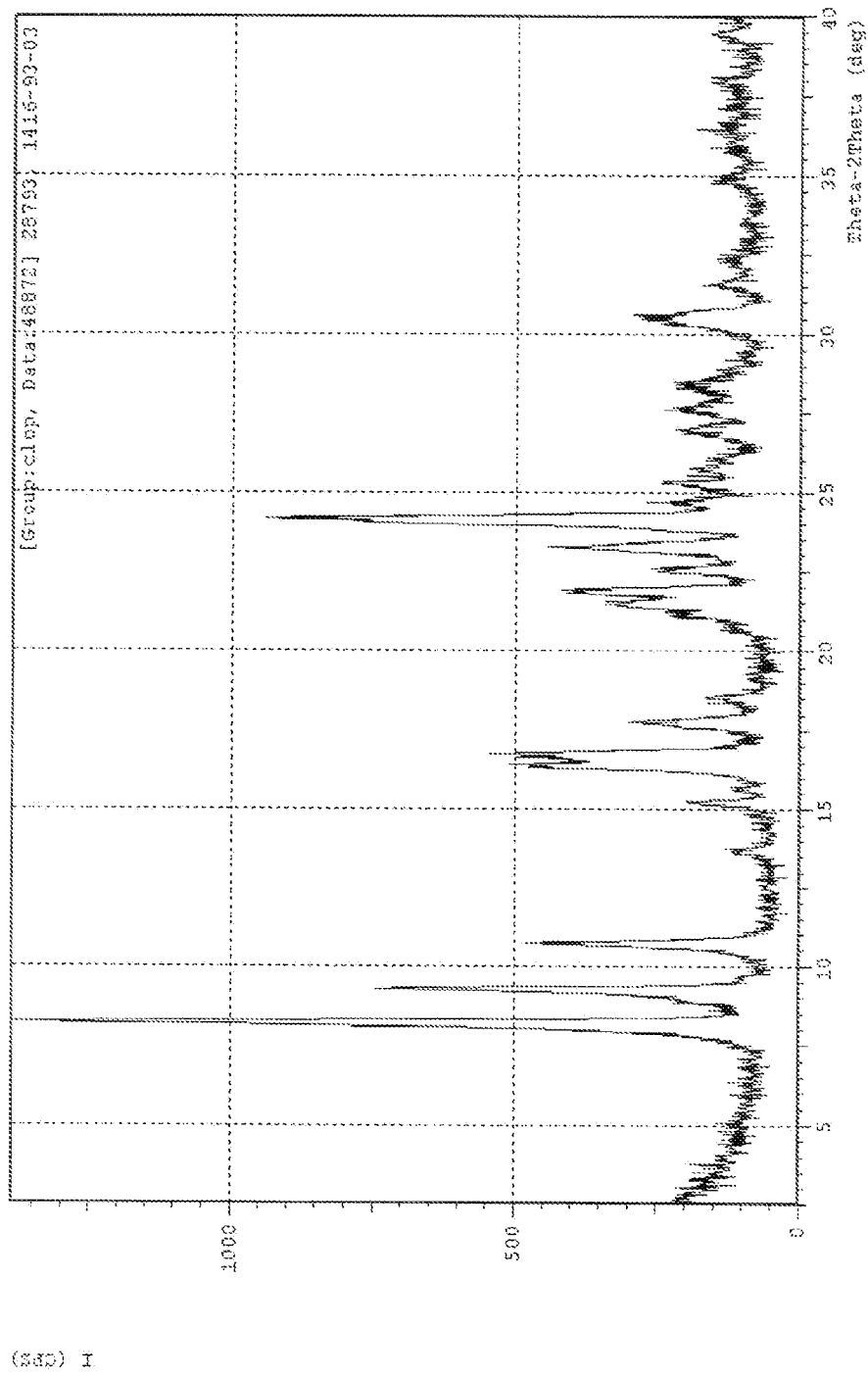
Figure 1D. XRPD pattern of Form D of methyl(+)-(S)-α-(2-chlorophenyl)-6,7-dihydrothieno[3,2-C]pyridine-5(4H) acetate naphthalene-1,5-disulfonate

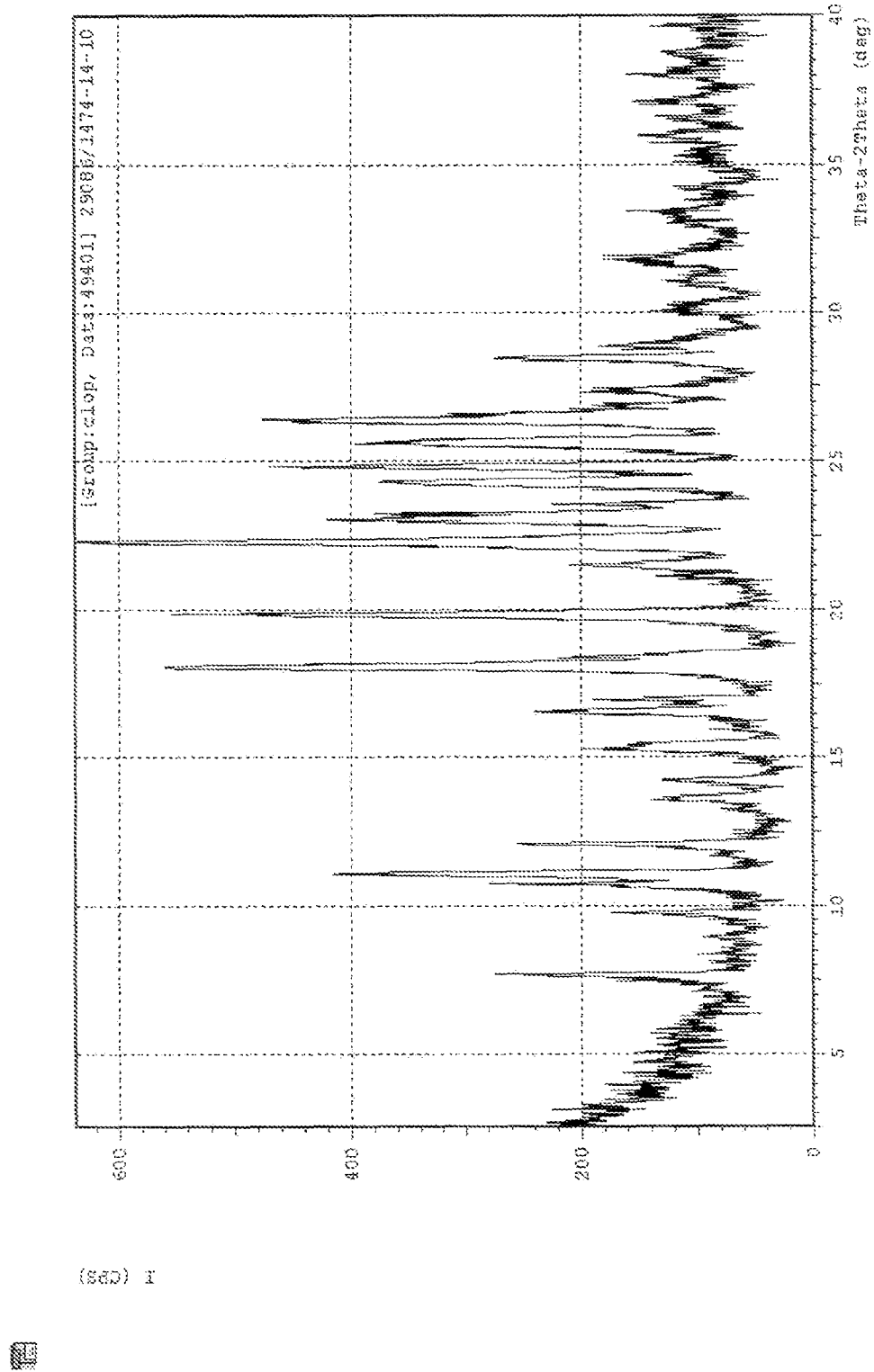
Figure 1E. XRPD pattern of Form E of methyl(+)-(S)-α-(2-chlorophenyl)-6,7-dihydrothieno[3,2-C]pyridine-5(4H) acetate naphthalene-1,5-disulfonate

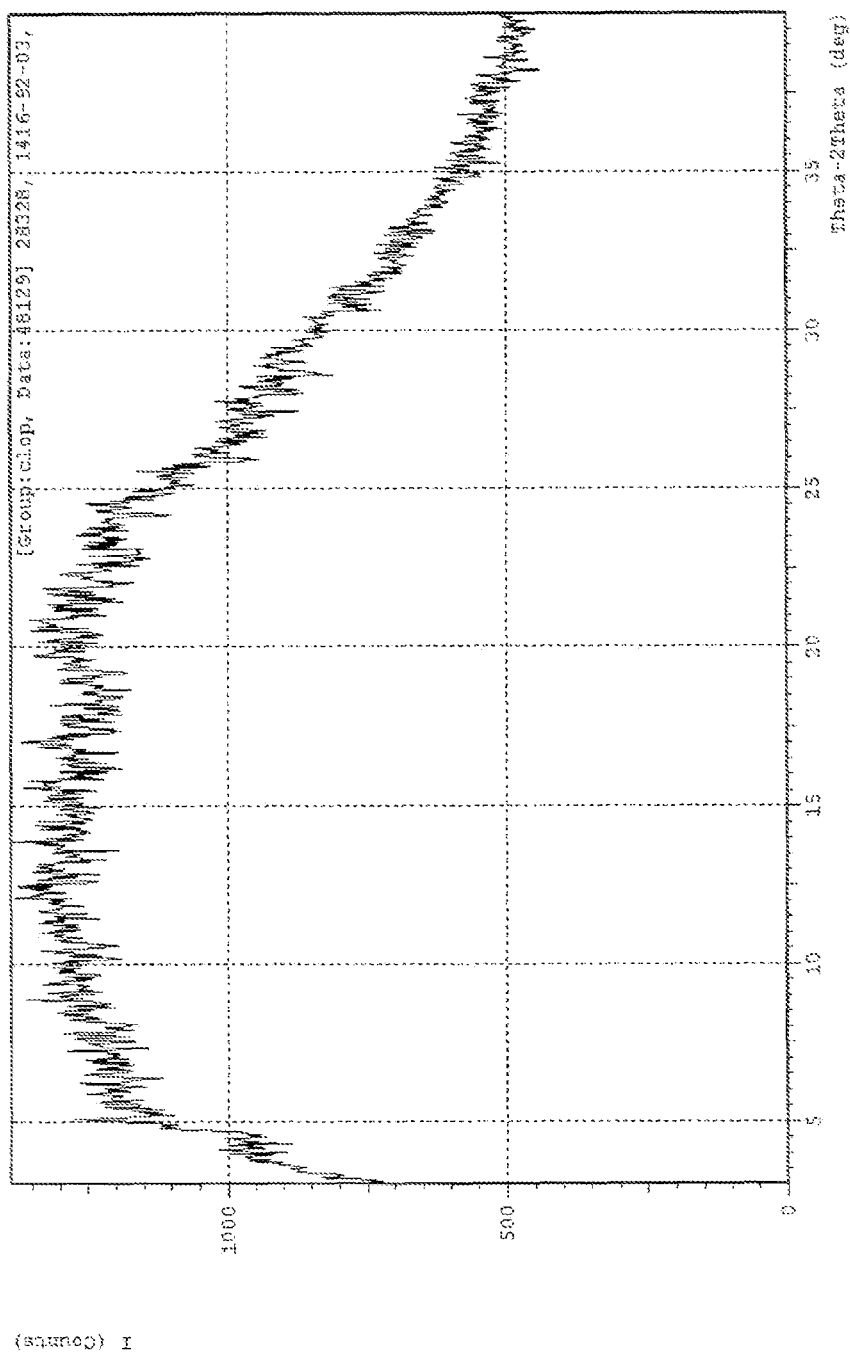
Figure 1F. XRPD pattern of Form F of methyl(+)-(S)-α-(2-chlorophenyl)-6,7-dihydrothieno[3,2-C]pyridine-5(4H) acetate naphthalene-1,5-disulfonate

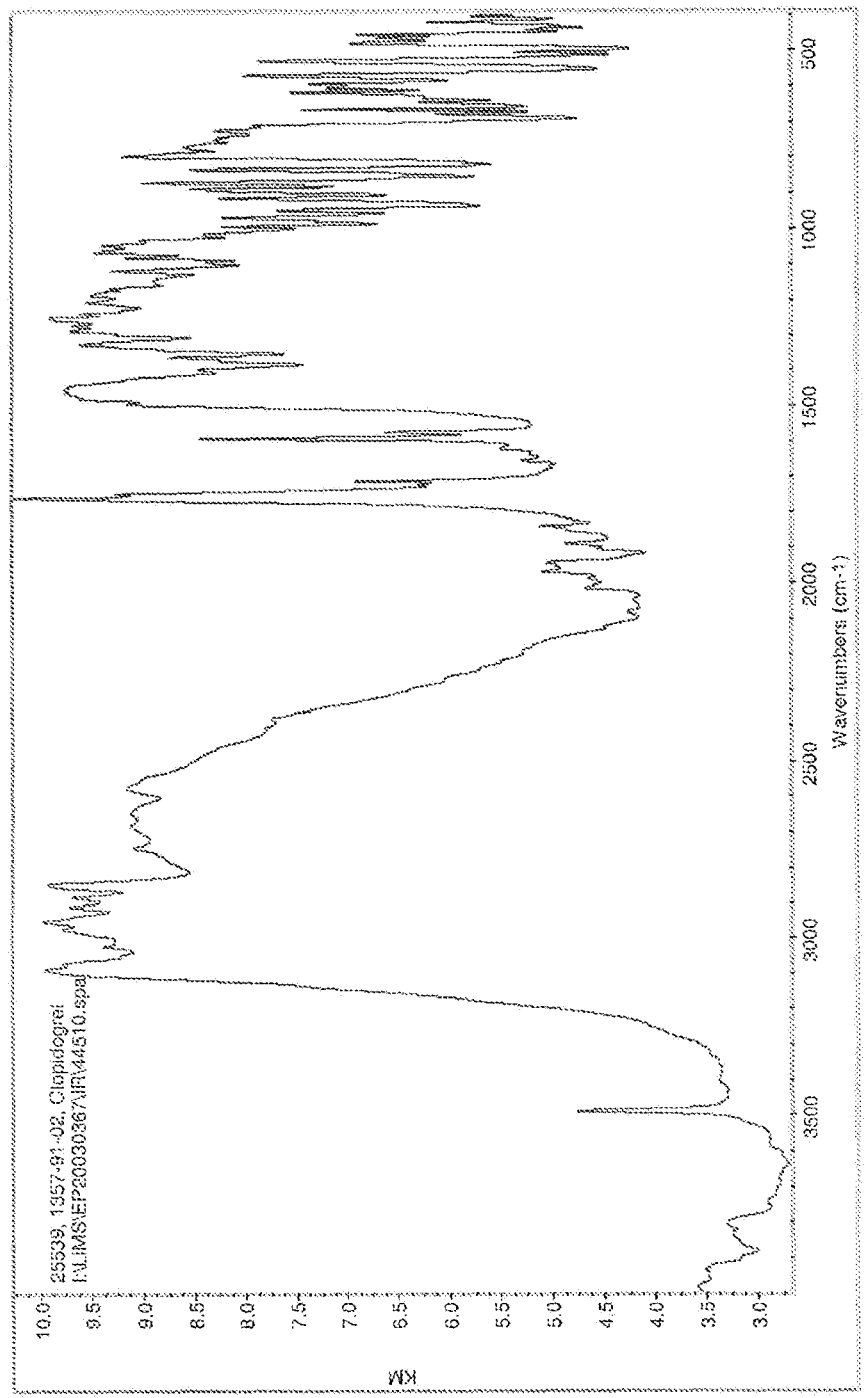
Figure 2. FT-IR spectrum of Form A of methyl(+)-(S)-α-(2-chlorophenyl)-6,7-dihydrothieno[3,2-C]pyridine-5(4H) acetate naphthalene-1,5-disulfonate

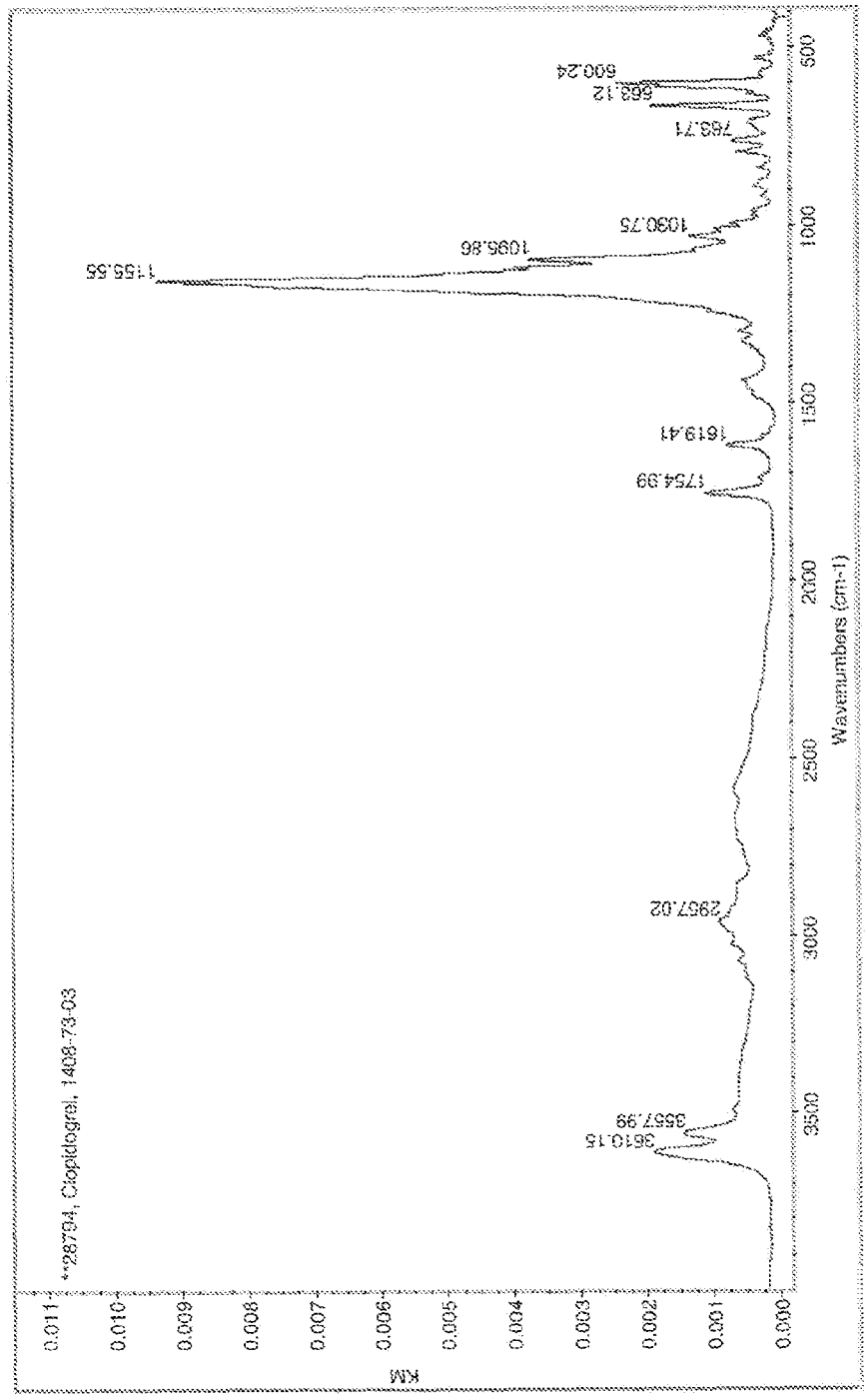
Figure 3. FT-IR spectrum of Form B of methyl(+)-(S)-α-(2-chlorophenyl)-6,7-dihydrothieno[3,2-C]pyridine-5(4H) acetate naphthalene-1,5-disulfonate

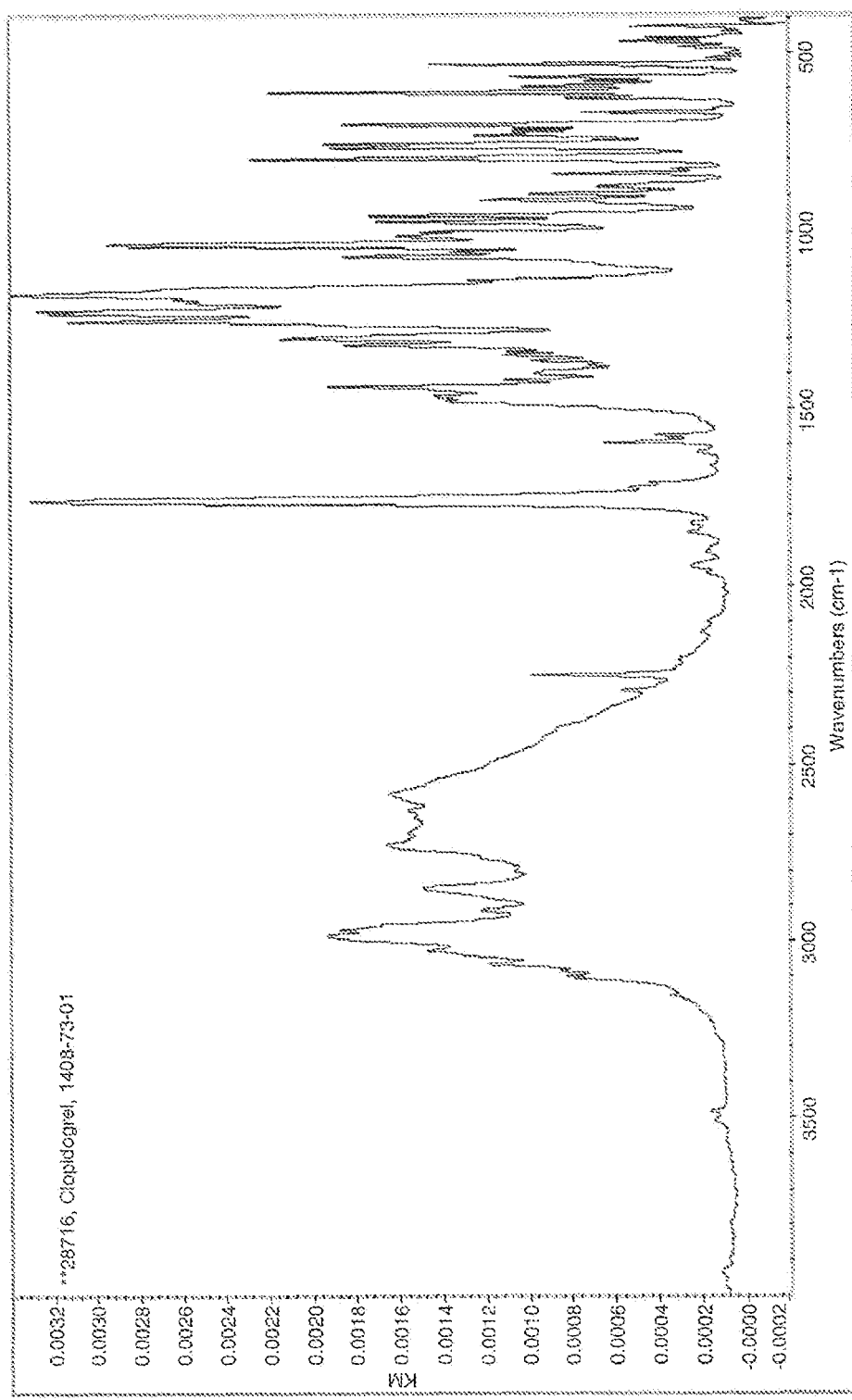
Figure 4. FT-IR spectrum of Form C of methyl(+)-(S)-α-(2-chlorophenyl)-6,7-dihydrothieno[3,2-C]pyridine-5(4H) acetate naphthalene-1,5-disulfonate

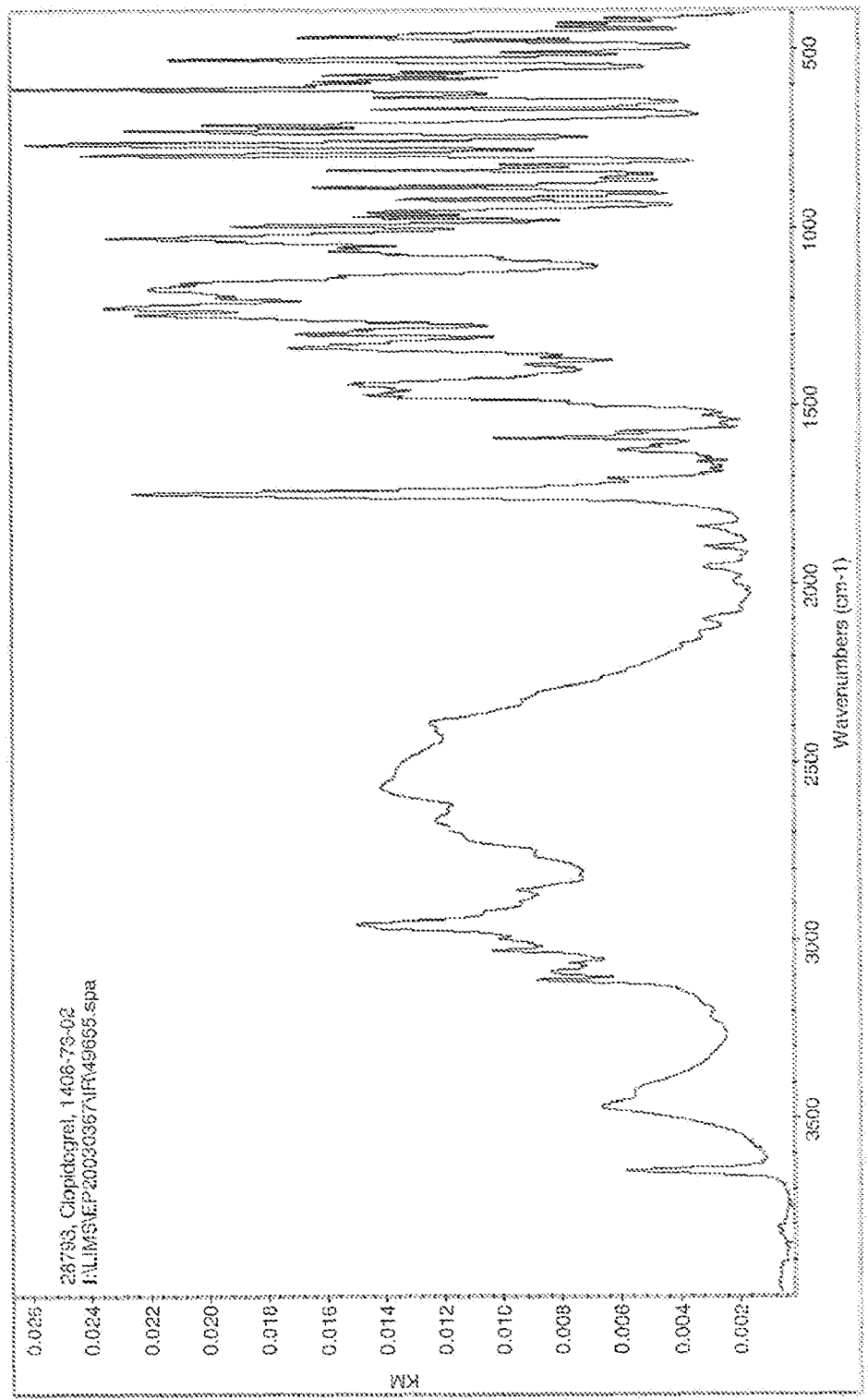
Figure 5. FT-IR spectrum of Form D of methyl(+)-(S)-α-(2-chlorophenyl)-6,7-dihydrothieno[3,2-C]pyridine-5(4H) acetate naphthalene-1,5-disulfonate

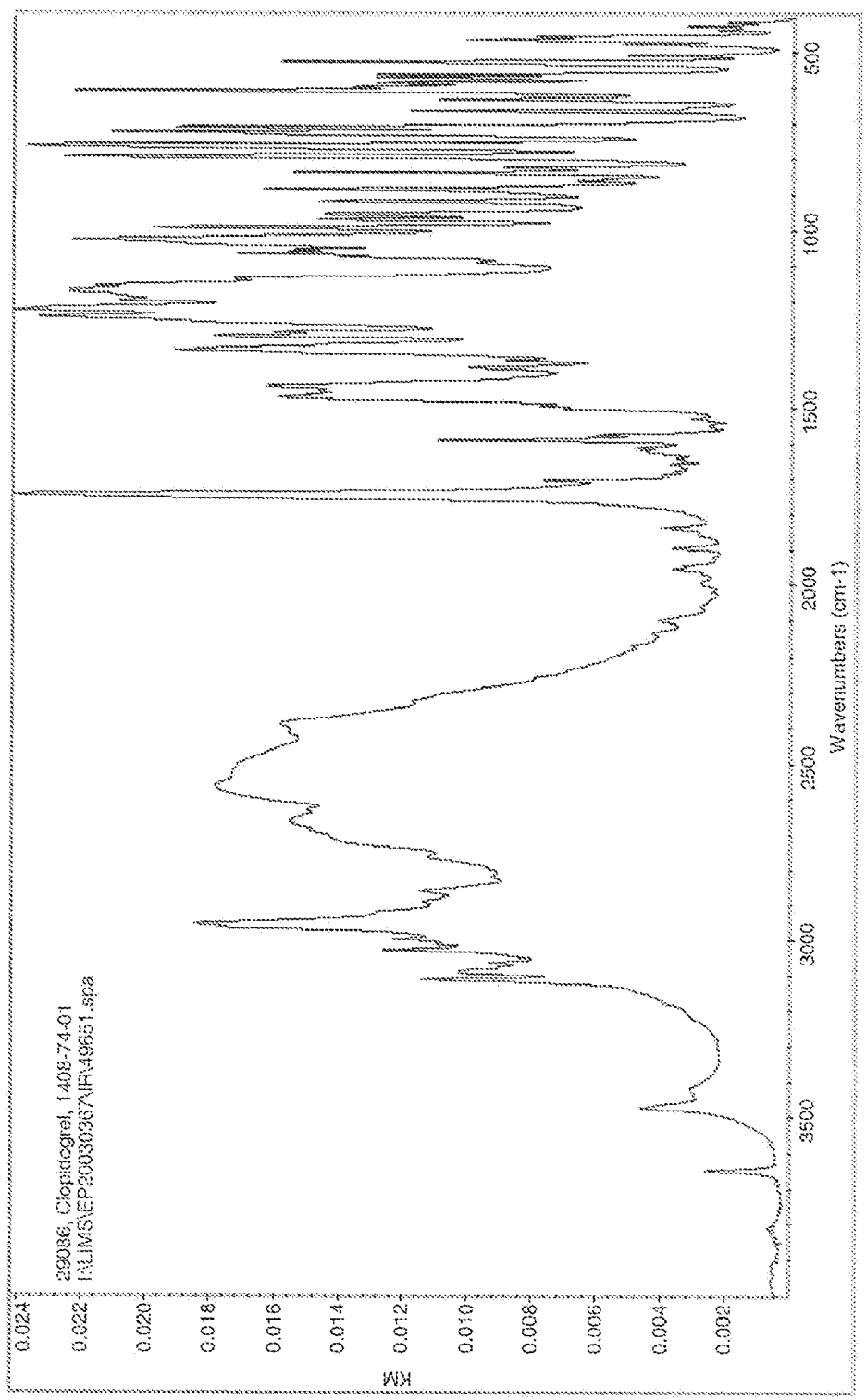
Figure 6. FT-IR spectrum of Form E of methyl(+)-(S)-α-(2-chlorophenyl)-6,7-dihydrothieno[3,2-C]pyridine-5(4H) acetate naphthalene-1,5-disulfonate

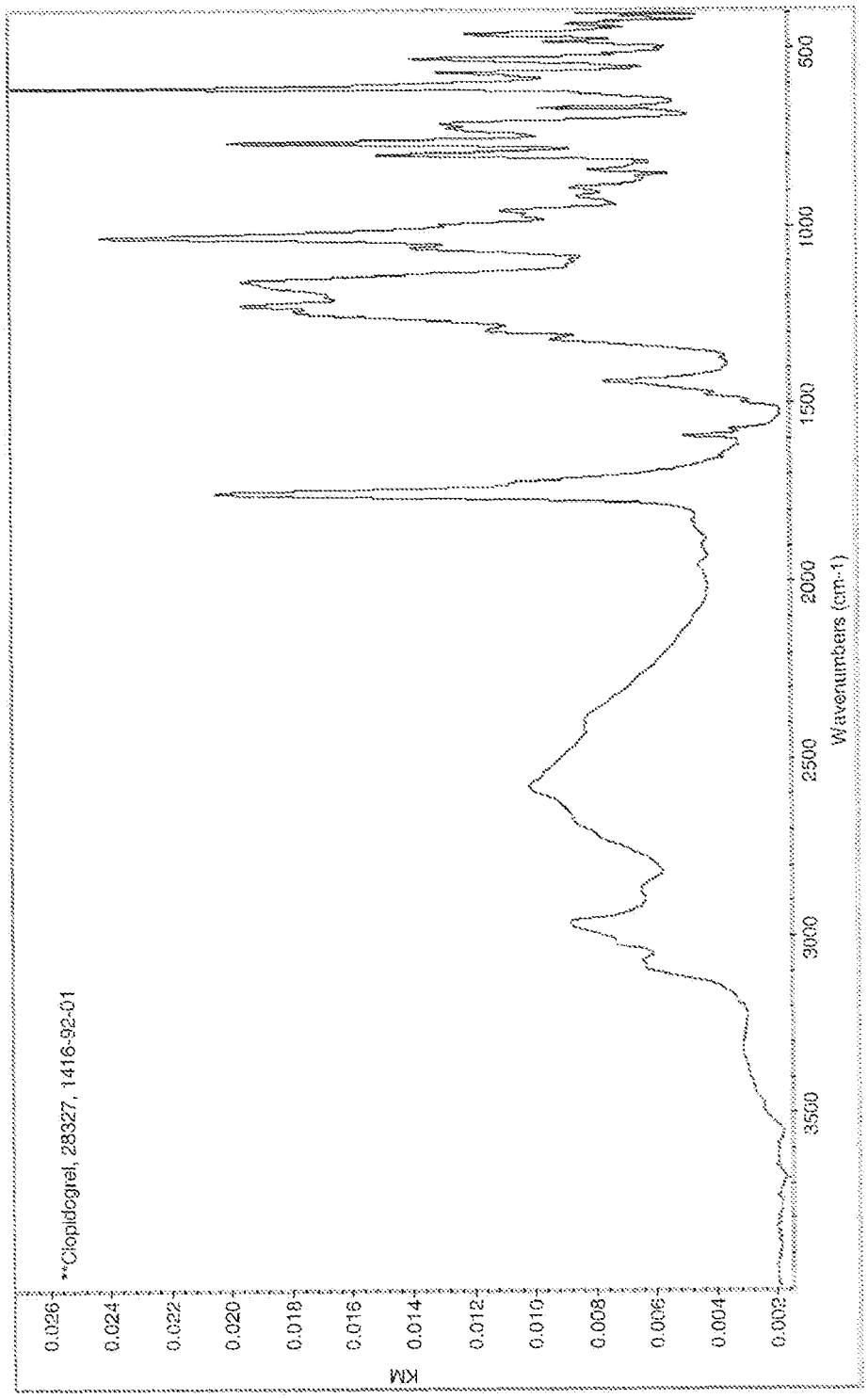
Figure 7. FT-IR spectrum of Form F of methyl(+)-(S)-α-(2-chlorophenyl)-6,7-dihydrothieno[3,2-C]pyridine-5(4H) acetate naphthalene-1,5-disulfonate

CLOPIDOGREL SALT AND POLYMORPHIC FORMS THEREOF

The invention relates to methyl(+)-(S)-α-(2-chlorophenyl)-6,7-dihydrothieno[3,2-C]pyridine-5(4H) acetate naphthalene-1,5-disulfonate, or a polymorphic form and/or a hydrate and/or a solvate thereof, to pharmaceutical compositions containing the same and to the method of use thereof for inhibiting platelet aggregation.

U.S. Pat. No. 4,847,265, issued Jul. 11, 1989, discloses the dextrorotatory enantiomer of methyl alpha-5-(4,5,6,7-tetrahydro-(3,2-C)thienopyridyl) (2-chlorophenyl)acetate or a pharmaceutically acceptable salt thereof. Specifically disclosed are the hydrochloride, hydrogen sulfate, hydrobromide, and taurocholate salts.

U.S. Pat. No. 6,429,210, issued Aug. 6, 2002, discloses polymorphic Form II of methyl(+)-(S)-α-(2-chlorophenyl)-6,7-dihydrothieno[3,2-C]pyridine-5(4H) acetate hydrogen sulfate known as clopidogrel hydrogen sulfate.

WO 03/066637, published Aug. 14, 2003, discloses crystalline Forms I and II of methyl-(S)-(+)-(2-chlorophenyl)-2-(6,7-dihydro-4H-thieno[3,2-C]pyridine-5-yl) acetate hydrochloride.

U.S. 2003/0114479, published Jun. 19, 2003, discloses crystalline Forms III, IV, and V, and an amorphous form of clopidogrel hydrogen sulfate.

U.S. 2003/0225129, published Dec. 4, 2003, discloses crystalline Forms III, IV, V and VI and amorphous form of clopidogrel hydrogen sulfate.

The solid state physical properties of a pharmaceutical compound can be influenced by the conditions under which the compound is obtained in solid form. Solid state physical properties include, for example, the flowability of the milled solid which affects the ease with which the compound is handled during processing into a pharmaceutical product. Another important solid state property of a pharmaceutical compound is its rate of dissolution in aqueous fluid. The rate of dissolution of an active ingredient in a patient's stomach fluid can have therapeutic consequences because it imposes an upper limit on the rate at which an orally administered active ingredient can reach the blood. The solid-state form of a compounds may also affect its solubility, bioavailability, behavior on compaction, stability, or its electrostatic nature.

These physical properties of a pharmaceutical compound can be influenced by the conformation and orientation of molecules in the unit cell which defines a particular polymorphic form of a compound. The polymorphic form may give rise to thermal behavior different from that of the amorphous material or another polymorphic form. Thermal behavior is measured in the laboratory by such techniques as capillary melting point, thermogravimetric analyses and differential scanning calorimetry and can be used to distinguish one polymorphic form from another. A particular polymorphic form may also give rise to distinct properties that may be detectable by X-ray powder diffraction, solid-state $^{13}$CNMR spectrometry and infrared spectrometry.

The discovery of new crystalline polymorphic or amorphous forms of a pharmaceutical compound provides an opportunity to improve the physical or performance characteristics of a pharmaceutical product in that it enlarges the repertoire of materials that a formulation scientist has available for designing, for example, a pharmaceutical dosage form of a drug with a targeted release profile or other desired characteristic.

The invention relates to methyl(+)-(S)-α-(2-chlorophenyl)-6,7-dihydrothieno[3,2-C]pyridine-5(4H) acetate naphthalene-1,5-disulfonate of the formula I:

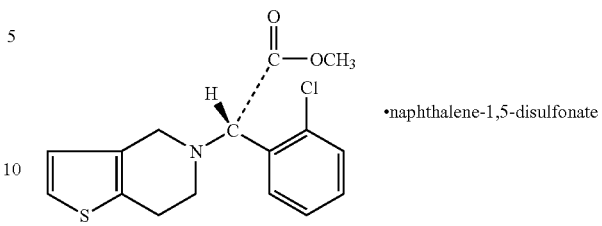

(I)

or a polymorphic form and/or a hydrate and/or a solvate thereof, and more particularly to polymorphic Forms A, B, C, D, E, and F of the compound.

Polymorphic Form A of methyl(+)-(S)-α-(2-chlorophenyl)-6,7-dihydrothieno[3,2-C]pyridine-5(4H) acetate naphthalene-1,5-disulfonate 1,4-dioxane is characterized by an X-ray powder diffraction pattern with a peak at about 11.7 degrees two-theta and more particularly with peaks at about 10.8, 11.7, and 13.0 degrees two-theta. Form A of methyl(+)-(S)-α-(2-chlorophenyl)-6,7-dihydrothieno[3,2-C]pyridine-5(4H) acetate naphthalene-1,5-disulfonate 1,4-dioxane is also characterized by an FTIR spectrum with peaks at about 1249, 1452, 1760, 2848, 2955, 3090, and 3490 cm$^{-1}$. Form A of methyl(+)-(S)-α-(2-chlorophenyl)-6,7-dihydrothieno[3,2-C]pyridine-5(4H) acetate naphthalene-1,5-disulfonate 1,4-dioxane, which has a melting point of about 165° C. exhibits an X-ray powder diffraction pattern substantially as depicted in FIG. 1A and an FTIR spectrum substantially as depicted in FIG. 2.

Polymorphic Form B of methyl(+)-(S)-α-(2-chlorophenyl)-6,7-dihydrothieno[3,2-C]pyridine-5(4H) acetate naphthalene-1,5-disulfonate hydrate is characterized by an X-ray powder diffraction pattern with a peak at about 13.4 degrees two-theta. Form B of methyl(+)-(S)-α-(2-chlorophenyl)-6,7-dihydrothieno[3,2C]pyridine-5(4H) acetate naphthalene-1, 5-disulfonate hydrate is also characterized by an FTIR spectrum with peaks at about 600, 663, 1096, 1156, 3557, and 3605 cm$^{-1}$. Form B of methyl(+)-(S)-α-(2-chlorophenyl)-6,7-dihydrothieno[3,2C]pyridine-5(4H) acetate naphthalene-1,5-disulfonate hydrate, which has a melting point of about 218° C., exhibits an X-ray powder diffraction pattern substantially as depicted in FIG. 1B and an FTIR spectrum substantially as depicted in FIG. 3.

Polymorphic Form C of methyl(+)-(S)-α-(2-chlorophenyl)-6,7-dihydrothieno[3,2-C]pyridine-5(4H) acetate naphthalene-1,5-disulfonate acetonitrile-hydrate is characterized by an X-ray powder diffraction pattern with a peak at about 8.7 degrees two-theta and more particularly with peaks at about 8.7, 14.1, and 27.4 degrees two-theta. Form C of methyl (+)-(S)-α-(2-chlorophenyl)-6,7-dihydrothieno[3,2-C]pyridine-5(4H) acetate naphthalene-1,5-disulfonate acetonitrile-hydrate is also characterized by an FTIR spectrum with peaks at about 529, 796, 1035, 1175, 1221, 1251, and 1759 cm$^{-1}$. Form C of methyl(+)-(S)-α-2-chlorophenyl)-6,7-dihydrothieno[3,2-C]pyridine-5(4H) acetate naphthalene-1,5-disulfonate acetonitrile-hydrate, which has a melting point of about 228° C., exhibits an X-ray powder diffraction pattern substantially as depicted in FIG. 1C and an FTIR spectrum substantially as depicted in FIG. 4.

Polymorphic Form D of methyl(+)-(S)-α-(2-chlorophenyl)-6,7-dihydrothieno[3,2-C]pyridine-5(4H) acetate naphthalene-1,5-disulfonate hydrate is characterized by an X-ray powder diffraction pattern with a peak at about 24.1 degrees two-theta and more particularly with peaks at about 9.3 and 24.1 degrees two-theta. Form D of methyl(+)-(S)-α-(2-chlorophenyl)-6,7-dihydrothieno[3,2-C]pyridine-5(4H) acetate naphthalene-1,5-disulfonate hydrate is also characterized by an FTIR spectrum with peaks about 525, 711, 1026, 1170, 1243, and 1746 cm$^{-1}$. Form D of methyl(+)-(S)-α-(2-chlorophenyl)-6,7-dihydrothieno[3,2-C]pyridine-5(4H) acetate naphthalene-1,5-disulfonate hydrate, which has a melting point of about 228° C., exhibits an X-ray powder diffraction pattern substantially as depicted in FIG. 1D and an FTIR spectrum substantially as depicted in FIG. 5.

Polymorphic Form E of methyl(+)-(S)-α-(2-chlorophenyl)-6,7-dihydrothieno[3,2-C]pyridine-5(4H) acetate naphthalene-1,5-disulfonate hydrate is characterized by an X-ray powder diffraction pattern with a peak at about 26.4 degrees two-theta and more particularly with peaks at about 7.6, 11.0, 12.1, and 26.4 degrees two-theta. Form E of methyl(+)-(S)-α-(2-chlorophenyl)-6,7-dihydrothieno[3,2-C]pyridine-5(4H) acetate naphthalene-1,5-disulfonate hydrate is also characterized by an FTIR spectrum with peaks a about 610, 764, 1026, 1196, 1224, and 1746 cm$^{-1}$. Form E of methyl(+)-(S)-α-(2-chlorophenyl)-6,7-dihydrothieno[3,2-C]pyridine-5(4H) acetate naphthalene-1,5-disulfonate hydrate, which has a melting point of about 224° C., exhibits an X-ray powder diffraction pattern substantially as depicted in FIG. 1E and an FTIR spectrum substantially as depicted in FIG. 6.

Polymorphic Form F of methyl(+)-(S)-α-(2-chlorophenyl)-6,7-dihydrothieno[3,2-C]pyridine-5(4H) acetate naphthalene-1,5-disulfonate is characterized by an FTIR spectrum with peaks at about 565, 610, 764, 1028, 1751, and 2579 cm$^{-1}$. Form F of methyl(+)-(S)-α-(2-chlorophenyl)-6,7-dihydrothieno[3,2-C]pyridine-5(4H) acetate naphthalene-1,5-disulfonate exhibits an X-ray powder diffraction pattern substantially as depicted in FIG. 1F and an FTIR spectrum substantially as depicted in FIG. 7

The present invention further relates to a pharmaceutical composition comprising: methyl(+)-(S)-α-(2-chlorophenyl)-6,7-dihydrothieno[3,2-C]pyridine-5(4H) acetate naphthalene-1,5-disulfonate or a polymorphic form and/or a hydrate and/or a solvate thereof, together with a pharmaceutically acceptable carrier, adjuvant, diluent, or vehicle.

The present invention further relates to a method for inhibiting platelet aggregation which comprises administering to a patient in need thereof an effective amount of methyl(+) - (S)-α-(2-chlorophenyl)-6,7-dihydrothieno[3,2-C]pyridine-5(4H) acetate naphthalene-1,5-disulfonate or a polymorphic form and/or a hydrate and/or a solvate thereof.

The present invention further relates to the use of methyl (+)-(S)-α-(2-chlorophenyl)-6,7-dihydrothieno[3,2-C]pyridine-5(4H) acetate naphthalene-1,5-disulfonate or a polymorphic form and/or a hydrate and/or a solvate thereof in the preparation of a medicament for inhibiting platelet aggregation.

The present invention further relates to a method of reducing atherosclerotic events which comprises administering to a patient in need thereof an effective amount of methyl (+) - (S)-α-(2-chlorophenyl)-6,7-dihydrothieno[3,2-C]pyridine-5(4H) acetate naphthalene-1,5-disulfonate or a polymorphic form and/or a hydrate and/or a solvate thereof.

The present invention further relates to the use of methyl (+)-(S)-α-(2-chlorophenyl)-6,7-dihydrothieno[3,2-C]pyridine-5(4H) acetate naphthalene-1,5-disulfonate or a polymorphic form and/or a hydrate and/or a solvate thereof in the preparation of a medicament for reducing atherosclerotic events.

FIG. 1A is an X-ray powder diffraction pattern of Form A of methyl(+)-(S)-α-(2-chlorophenyl)-6,7-dihydrothieno[3,2-C]pyridine-5(4H) acetate naphthalene-1,5-disulfonate 1,4-dioxane.

FIG. 1B is an X-ray powder diffraction pattern of Form B of methyl(+)-(S)-α-(2-chlorophenyl)-6,7-dihydrothieno[3,2-C]pyridine-5(4H) acetate naphthalene-1,5-disulfonate hydrate.

FIG. 1C is an X-ray powder diffraction pattern of Form C of methyl(+)-(S)-α-(2-chlorophenyl)-6,7-dihydrothieno[3,2-C]pyridine-5(4H) acetate naphthalene-1,5-disulfonate acetonitrile hydrate.

FIG. 1D is an X-ray powder diffraction pattern of Form D of methyl(+)-(S)-α-(2-chlorophenyl)-6,7-dihydrothieno[3,2-C]pyridine-5(4H) acetate naphthalene-1,5-disulfonate hydrate.

FIG. 1E is an X-ray powder diffraction pattern of Form E of methyl(+)-(S)-α-(2-chlorophenyl)-6,7-dihydrothieno[3,2-C]pyridine-5(4H) acetate naphthalene-1,5-disulfonate hydrate.

FIG. 1F is an X-ray powder diffraction pattern of Form F of methyl(+)-(S)-α-(2-chlorophenyl)-6,7-dihydrothieno[3,2-C]pyridine-5(4H) acetate naphthalene-1,5-disulfonate.

FIG. 2 is an FTIR spectrum of Form A of methyl(+)-(S)-α-(2-chlorophenyl)-6,7-dihydrothieno[3,2-C]pyridine-5(4H) acetate naphthalene-1,5-disulfonate 1,4-dioxane.

FIG. 3 is an FTIR spectrum of Form B of methyl(+)-(S)-α-(2-chlorophenyl)-6,7-dihydrothieno[3,2-C]pyridine-5(4H) acetate naphthalene-1,5-disulfonate hydrate.

FIG. 4 is an FTIR spectrum of Form C of methyl(+)-(S)-α-(2-chlorophenyl)-6,7-dihydrothieno[3,2-C]pyridine-5(4H) acetate naphthalene-1,5-disulfonate acetonitrile-hydrate.

FIG. 5 is an FTIR spectrum of Form D of methyl(+)-(S-α-(2-chlorophenyl)-6,7-dihydrothieno[3,2-C]pyridine-5(4H) acetate naphthalene-1,5-disulfonate hydrate.

FIG. 6 is an FTIR spectrum of Form E of methyl(+)-(S)-α-(2-chlorophenyl)-6,7-dihydrothieno[3,2-C]pyridine-5(4H) acetate naphthalene-1,5-disulfonate hydrate.

FIG. 7 is an FTIR spectrum of Form F of methyl(+)-(S)-α-(2-chlorophenyl)-6,7-dihydrothieno[3,2-C]pyridine-5(4H) acetate naphthalene-1,5-disulfonate.

Form A of methyl(+)-(S)-α-(2-chlorophenyl)-6,7-dihydrothieno[3,2-C]pyridine-5(4H) acetate naphthalene-1,5-disulfonate 1,4-dioxane may be prepared by adding a solution of methyl(+)-(S)-α-(2-chlorophenyl)-6,7-dihydrothieno[3,2-C]pyridine-5(4H) acetate in ethanol to a solution of naphthalene-1,5-disulfonic acid in ethanol and then adding heptane to the mixture. The solvents are evaporated, the residue is slurried with 1,4-dioxane/ethanol and the solvents are evaporated to afford Form A.

Form B of methyl(+)-(S)-α-(2-chlorophenyl)-6,7-dihydrothieno[3,2-C]pyridine-5(4H) acetate naphthalene-1,5-disulfonate hydrate may be prepared by adding methyl (+)-(S)-α-(2-chlorophenyl)-6,7-dihydrothieno[3,2-C]pyridine-5(4H) acetate to a solution of naphthalene-1,5-disulfonic acid in ethanol, followed by the addition of 1,4,dioxane. Evaporation of the solvent affords a residue, that is seeded with Form A of the compound and dissolved in ethanol and then 1,4-dioxane is added followed by additional seeds of Form A. The solvents are evaporated and the residue is crystallized from acetone to afford Form B.

Form C of methyl(+)-(S)-α-(2-chlorophenyl)-6,7-dihydrothieno[3,2-C]pyridine-5(4H) acetate naphthalene-1,5-disulfonate acetonitrile hydrate may be prepared by dissolving Form B of the compound in acetonitrile at about 45° C. and collecting the Form C that precipitates upon cooling to room temperature.

Form D of methyl(+)-(S)-α-(2-chlorophenyl)-6,7-dihydrothieno[3,2-C]pyridine-5(4H) acetate naphthalene-1,5-disulfonate hydrate may be prepared by dissolving Form B of the compound in ethanol and collecting the Form D that precipitates upon cooling to about 0° C.

Form E of methyl(+)-(S)-α-(2-chlorophenyl)-6,7-dihydrothieno[3,2-C]pyridine-5(4H) acetate naphthalene-1,5-disulfonate hydrate may be prepared by subjecting Form A of the compound to 75% relative humidity at about 40° C. for about two (2) weeks.

Form F of methyl(+)-(S)-α-(2-chlorophenyl)-6,7-dihydrothieno[3,2-C]pyridine-5(4H) acetate naphthalene-1,5-disulfonate may be prepared by dissolving Form B of the compound in acetonitrile and collecting the Form F that precipitates by vapor diffusion upon placing a vial of the solution thus formed in a vial containing isopropylacetate.

Methyl(+)-(S)-α-(2-chlorophenyl)-6,7-dihydrothieno[3,2-C]pyridine-5(4H) acetate can be prepared, for example, by the method described in U.S. Pat. No. 4,847,265, which is incorporated herein by reference, or by the methods described herein in the examples.

The following examples will further illustrate the invention with, however, limiting it thereto. All melting points are given in degrees centigrade (° C.) and are obtained by placing the sample in a glass capillary. X-ray powder diffraction (XRPD) analyses were performed using a Shimadzu XRD-6000 (with a tube voltage of 40 kV, an amperage of 40 mA, divergence and scattering slits set at 1°, the receiving slit set at 0.15 mm, and a theta two theta continuous scan at 3°/min from 2.5 to 40° 2 theta) X-ray powder diffractometer using CuKα radiation. Infrared spectrum were acquired on a Magna-IR 860 Fourier transform infrared (FT-IR) spectrophotometer equipped with an Ever-Glo mid/far IR source, and the samples were prepared by mixing the sample with KBr.

Preparation 1

Methyl(+)-(S)-α-(2-chlorophenyl)-6,7-dihydrothieno[3,2-C]pyridine-5(4H) acetate

A solution of clopidogrel hydrogensulfate (which can be prepared according to the methods described in U.S. Pat. No. 6,429,210 the contents of which are incorporated herein by reference) was treated with an aqueous solution of sodium carbonate. The title compound was extracted with diethyl ether and the solution was dried over $MgSO_4$ and the solvent was removed under reduced pressure to afford the title compound as a yellow gel.

EXAMPLE 1

Form A of methyl(+)-(S)-α-(2-chlorophenyl)-6,7-dihydrothieno[3,2-C]pyridine-5(4H) acetate naphthalene-1,5-disulfonate 1,4-dioxane A solution of methyl(+)-(S)-α-(2-chlorophenyl)-6,7-dihydrothieno[3,2-C]pyridine-5(4H) acetate of preparation 1 (1.8067 g in 25 mL of ethanol) (2.767 mL) was added to a naphthalene-1,5-disulfonic acid solution (1.0498 g in 10 mL if ethanol) (1.066 mL), followed by heptane (1.60 mL). The solution was filtered through a 0.2 μm nylon filter into a clean vial and left to evaporate under nitrogen. A gel formed which was slurried in a 1,4-dioxane-ethanol (9:1) mixture (1.0 mL). The sample was then covered with Parafilm, perforated and allowed to evaporate. The solids which formed were temperature cycled between 25-35° C., filtered and dried to afford 0.2408 g of the title compound, m.p. 165° C., which was analyzed by FTIR and XRPD.

EXAMPLE 2

Form B of methyl(+)-(S)-α-(2-chlorophenyl)-6,7-dihydrothieno[3,2-C]pyridine-5(4H) acetate naphthalene-1,5-disulfonate Hydrate Methyl(+)-(S)-α-(2-chlorophenyl)-6,7-dihydrothieno[3,2-C]pyridine-5(4H) acetate of preparation 1 (1.3013 g) was added to a naphthalene-1,5-disulfonic acid solution in ethanol (1.0498 g in 10 mL of ethanol, 7.00 mL). Additional ethanol (3.00 mL) was added and mixture sonicated until complete dissolution was achieved. 1,4-Dioxane (10.0 mL) was added and the solution was filtered through a 0.2 μm nylon filter into a clean vial. The sample was left to evaporate uncovered. A gel formed which was seeded with Form A of Example 1, followed by the addition of ethanol (1 mL). The mixture was slurried at 40° C. until it completely dissolved. 1,4-Dioxane (8 mL) was added, followed by seeds of Form A of Example 1 and the mixture left to evaporate uncovered. White solids and gel formed and heptane (3.0 mL) was added. The slurry was filtered and solids washed with acetone. Some of the solids (0.0923 g) were slurried in acetone (0.80 mL) at 45° C. The slurry completely dissolved so more of the solids were added and the mixture was slurried at 45-46° C. The slurry was then filtered through a 0.2 μm nylon filter into a clean vial, capped, and placed in a water bath at 54° C., which was then slowly cooled to ambient temperature. Solids precipitated and the mixture was refrigerated, then filtered through a 0.2 μm filter, and solids left in the vial were dried under nitrogen to afford the title compound, m.p. 218° C., which was analyzed by FTIR and XRPD.

EXAMPLE 3

Form C of methyl(+)-(S)-α-(2-chlorophenyl)-6,7-dihydrothieno[3,2-C]pyridine-5(4H) acetate naphthalene-1,5-disulfonate acetonitrile-hydrate Form B of methyl(+)-(S)-α-(2-chlorophenyl)-6,7-dihydrothieno[3,2-C]pyridine-5(4H) acetate naphthalene-1,5-disulfonate hydrate of Example 2 (0.1151 g) was slurried in acetonitrile (0.800 mL) at 45° C. Once the slurry dissolved, additional compound of Example 2 was added. The title compound precipitated from solution after slowly being cooled to room temperature to afford the title compound, m.p. 228° C., which was analyzed by FTIR and XRPD.

EXAMPLE 4

Form D of methyl(+)-(S)-α-(2-chlorophenyl)-6,7-dihydrothieno[3,2-C]pyridine-5(4H) acetate naphthalene-1,5-disulfonate hydrate Form B of methyl(+)-(S)-α-(2-chlorophenyl)-6,7-dihydrothieno[3,2-C]pyridine-5(4H) acetate naphthalene-1,5-disulfonate hydrate of Example 2 (0.1074 g) was slurried in ethanol (0.80 mL). Additional compound of Example 2 was added once the slurry completely dissolved. Solids precipitated from the slow cooled solution in a freezer to afford the title compound, m.p. 228° C., which was analyzed by FTIR and XRPD.

EXAMPLE 5

Form E of methyl(+)-(S)-α-(2-chlorophenyl)-6,7-dihydrothieno[3,2-C]pyridine-5(4H) acetate naphthalene-1,5-disulfonate hydrate Form A of methyl(+)-(S)-α-(2-chlorophenyl)-6,7-dihydrothieno[3,2-C]pyridine-5(4H) acetate naphthalene-1,5-disulfonate hydrate 1,4-dioxane of Example 1 (0.0208 g) was placed in a 75% relative humidity chamber at 40° C. for two weeks to afford 0.0197 g of the title compound, m.p. 224° C., which was analyzed by FTIR and XRPD.

EXAMPLE 6

Form F of methyl(+)-(S)-α-(2-chlorophenyl)-6,7-dihydrothieno[3,2-C]pyridine-5(4H) acetate naphthalene-1,5-disulfonate Form B of methyl(+)-(S)-α-(2-chlorophenyl)-6,7-dihydrothieno[3,2-C]pyridine-5(4H) acetate naphthalene-1,5-disulfonate hydrate of Example 2 (0.0616 g) was dissolved in acetonitrile (1.0 mL) with sonication. The solution was filtered through a 0.2 μm nylon filter into a clean vial which was placed in a larger vial containing isopropylacetate (2.0 mL). The larger vial was capped and crystallization was afforded by vapor diffusion to afford the title compound in the form of an amorphous solid which was analyzed by FTIR and XRPD.

As disclosed in U.S. Pat. No. 4,847,265 and U.S. Pat. No. 5,576,328 (the entire contents of each of which is incorporated herein by reference) methyl(+)-(S)-α-(2-chlorophenyl)-6,7-dihydrothieno[3,2-C]pyridine-5(4H) acetate and its pharmaceutically acceptable salts have been found to possess valuable pharmacological properties. In particular, they have been found to inhibit platelet aggregation and thus would be useful in reducing atherosclerotic events, such as myocardial infarction, stroke, and vascular death.

The compounds of the invention are generally administered to patients which include, but are not limited to, mammals such as, for example, man. It will also be apparent to those skilled in the art that a compound according to the invention can be coadministered with other therapeutic or prophylactic agents and/or medicaments that are not medically incompatible therewith.

The compounds of the invention can be prepared for pharmaceutical use by conventional pharmaceutical procedures that are well known in the art, that is, by formulating a pharmaceutical composition which comprises compounds of the invention together with one or more pharmaceutically acceptable carriers, adjuvants, diluents or vehicles, for oral administration in solid or liquid form, parenteral administration, topical administration, rectal administration, or aerosol inhalation administration, and the like.

Solid compositions for oral administration include compressed tablets, pills, powders and granules. In such solid compositions, the active compound is admixed with at least one inert diluent such as starch, calcium carbonate, sucrose or lactose. These compositions may also contain additional substances other than inert diluents, e.g., lubricating agents, such as magnesium stearate, talc and the like.

Liquid compositions for oral administration include pharmaceutically acceptable emulsions, solutions, suspensions, syrups and elixirs containing inert diluents commonly used in the art, such was water and liquid paraffin. Besides inert diluents, such compositions may also contain adjuvants, such as, wetting and suspending agents and sweetening, flavoring, perfuming, and preserving agents. According to the invention, the compounds for oral administration also include capsules of absorbable material, such as gelatin, containing said active component with or without the addition of diluents or excipients.

Preparations according to the invention for parenteral administration include sterile aqueous, aqueous-organic, and organic solutions, suspensions and emulsions. Examples of organic solvents, or suspending media are propylene glycol, polyethylene glycol, vegetable oils such as olive oil and injectable organic esters such as ethyl oleate. These compositions can also contain adjuvants such as stabilizing, preserving, wetting, emulsifying and dispersing agents.

Preparations according to the invention for topical administration or aerosol inhalation administration include dissolving or suspending a compound of the invention in a pharmaceutically acceptable vehicle such as water, aqueous alcohol, glycol, oil solution or oil-water emulsion, and the like.

Preparations according to the invention for rectal administration include suppositories prepared by using suitable carriers, e.g., cacao butter, hardened oils, glycerides or saturated fatty acids, and the like.

If desired, the compounds of the invention can further be incorporated into slow release or targeted delivery systems such as polymer matrices, liposomes, and microspheres.

The percentage of active component in such compositions may be varied so that a suitable dosage is obtained. The dosage administered to a particular patient is variable depending upon the clinician's judgment using as criteria: the route of administration, the duration of treatment, the size and physical condition of the patient, the potency of the active component, and the patient's response thereto. An effective dosage amount of the active component can thus readily be determined by the clinician after a consideration of all criteria and using his best judgment on the patient's behalf. In general, a compound of the instant invention is administered at a dose in the range of about 0.01 to about 100 mg/kg body weight.

What is claimed is:

1. Polymorphic Form A of methyl(+)-(S)-α-(2-chlorophenyl)-6,7-dihydrothieno[3,2-C]pyridine-5(4H) acetate naphthalene-1,5-disulfonate 1,4-dioxane made by the process comprising the steps of:
   a) Combining methyl(+)-(S)-α-(2-chlorophenyl)-6,7-dihydrothieno[3,2-C]pyridine-5(4H) acetate and naphthalene-1,5-disulfonic acid in a solution of ethanol followed by addition of heptane;
   b) Filtering the solution formed in step a) through a 0.2 μm nylon filter into a clean vial;
   c) Evaporating the solvent under nitrogen;
   d) Slurrying the gel formed in step c) in a 1,4-dioxane-ethanol (9:1) mixture;
   e) Covering the slurry of step d) with perforated parafilm and allowing the 1,4-dioxane-ethanol mixture to evaporate;
   f) Temperature cycling the solids formed in step e) between 25-35° C.; and
   g) Filtering and drying the solids formed in step f),
   wherein the Polymorphic Form A of methyl(+)-(S)-α-(2-chlorophenyl)-6,7-dihydrothieno[3,2-C]pyridine-5(4H) acetate naphthalene-1,5-disulfonate 1,4-dioxane made by steps a)-g) has an X-ray powder diffraction pattern with peaks at 10.8 (Intensity=50%), 11.7 (Intensity=48%), and 13.0 (Intensity=64.5%) degrees two-theta, an FTIR spectrum with peaks at about 1249, 1452, 1760, 2848, 2955, 3090, and 3490 $cm^{-1}$, and a melting point of 165° C.

* * * * *

UNITED STATES PATENT AND TRADEMARK OFFICE
CERTIFICATE OF CORRECTION

PATENT NO. : 7,652,139 B2  Page 1 of 1
APPLICATION NO. : 11/550865
DATED : January 26, 2010
INVENTOR(S) : Keith Richard Lorimer et al.

It is certified that error appears in the above-identified patent and that said Letters Patent is hereby corrected as shown below:

On the Title page, item (56); under "Other Publications", in column 2, line 1, delete "Britian," and insert -- Britain, --, therefor.

In column 1, line 3, below "FORMS THEREOF",
insert -- CROSS-REFERENCE TO RELATED APPLICATIONS --.

In column 1, line 28, before "amorphous" insert -- an --.

In column 1, line 42, delete "compounds" and insert -- compound --, therefor.

In column 1, line 51, delete "anlyses" and insert -- analysis --, therefor.

In column 2, line 43, delete "[3,2C]" and insert -- [3,2-C] --, therefor.

In column 3, line 21, delete "a" and insert -- at --, therefor.

In column 3, line 45-46, delete "methyl(+)  -(S)" and insert -- methyl(+)-(S) --, therefor.

In column 3, line 58, delete "methyl(+)  -(S)" and insert -- methyl(+)-(S) --, therefor.

In column 6, line 11, delete "Hydrate" and insert -- hydrate --, therefor.

In column 7, line 65, delete "was" and insert -- as --, therefor.

Signed and Sealed this

Third Day of August, 2010

David J. Kappos
*Director of the United States Patent and Trademark Office*